(12) United States Patent
Zisapel et al.

(10) Patent No.: US 8,309,767 B2
(45) Date of Patent: Nov. 13, 2012

(54) 2-AMINOBENZOYL DERIVATIVES

(75) Inventors: Nava Zisapel, Tel Aviv (IL); Moshe Laudon, Kfar Saba (IL); Dvorah Daily, Herzliya (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 326 days.

(21) Appl. No.: 10/562,197

(22) PCT Filed: Jun. 24, 2004

(86) PCT No.: PCT/IL2004/000567
§ 371 (c)(1),
(2), (4) Date: May 9, 2006

(87) PCT Pub. No.: WO2004/112690
PCT Pub. Date: Dec. 29, 2004

(65) Prior Publication Data
US 2006/0270733 A1    Nov. 30, 2006

(30) Foreign Application Priority Data

Jun. 26, 2003 (IL) .......................................... 156669

(51) Int. Cl.
*C07C 225/22* (2006.01)
*C07C 205/06* (2006.01)
*A61K 31/04* (2006.01)

(52) U.S. Cl. ........ 564/342; 564/441; 562/435; 514/564; 514/649

(58) Field of Classification Search ........................ None
See application file for complete search history.

(56) References Cited

U.S. PATENT DOCUMENTS 4,018,823 A    4/1977    Schwan
4,816,489 A    3/1989    Lafon

FOREIGN PATENT DOCUMENTS

GB    1334884    10/1973
JP    49-101348 A    9/1974

OTHER PUBLICATIONS

Database CAPLUS on STN, Acc. No. 1921:18616, Gabriel et al., Berichte der Deutschen Chemischen Gesellschaft [Abteilung] B: Abhandlungen (1921), 54B, p. 1067-78 (abstract).*
Database CAPLUS on STN, Acc. No. 1952:54561, Dalgliesh, J. of the Chem. Soc. 91952), p. 137-141 (abstract).*
Database CAPLUS on STN, Acc. No. 1941:35120, de Diesbach et al., Helvetica Chimica Acta (1941), 24, p. 158-173 (abstract).*
Database CAPLUS on STN, Acc. No. 1986:572056, Lafon, FR 2569185 A1 (Feb. 21, 1986) (abstract).*
Database CAPLUS on STN, Acc. No. 1993:428417, Gellerman et al., Tetrahedron Letters (1993), 34(11), p. 1827-1830 (abstract).*
Database CAPLUS on STN, Acc. No. 1979:104026, Kuwata et al., JP 53111093 A (Sep. 28, 1978) (abstract).*
Database CAPLUS on STN, Acc. No. 1964:425097, Runti et al., Bollettino Chimico Farmaceutico (1964), 103(3), p. 165-170 (abstract).*
Database CAPLUS on STN, Acc. No. 1976:508614, Taylor et al., Journal of the Chemical Society, Perkin Transactions 1: Organic and Bio-Organic Chemistry (1972-1999) (1976), 12, 1331-1338 (CAPLUS abstract).*
Database CAPLUS on STN, Acc. No. 1965:440217, Hopsu et al., Annales Medicinae Experimentalis et Biologiae Fenniae (1965), 43(2), p. 106-113 (abstract).*
Back, W., "Synthesis of O-acylamino-beta-aminopropiophenones," Archiv. der Pharmazie und Berichte der Deutschen Pharmazeutischen Gesellschaft, 1972, pp. 448-455, vol. 305(6). Stn. Cas Online Abstract No. 1972:474963.
Bhat, A.R., "Synthesis and Biological Activities of Mannich Bases of 5-Amino Acenaphthene," J. Inst. Chemists (India), vol. 57, pp. 195-196 (Sep. 1985).
Nemeth, H., et al., "Kynurenines, Parkinson's disease and other neurodegenerative disorders: preclinical and clinical studies," J. Neural. Transm. Suppl., 70: 285-304 (2006) (Abstract).
Gellerman, Gari, et al., "The Biominetic Synthesis of Marine Alkaloid Related Pyrido- and Pyrrolo[2,3,4,-kl] acridines," Tetrahedron, 50(45): 12959-12972 (1994).
Joh, Yoshinori, et al., "Synthesis of 5-Hydroxykynuramine Hydrochloride (Mausannine)," The Journal of Biochemistry, 58(3): 248-250 (1965).
Moon, Byoungho, et al., "Structure and Bioactivity of Erebusinone, a Pigment from the Antarctic Sponge Isodictya erinacea," Tetrahedron 56(46): 9057-9062 (2000).
Schwarcz, R., et al., "Manipulation of Brain Kynureines: Glial Targets, Neuronal Effects, and Clinical Opportunities," Journal of Pharmacology and Experimental Therapeutics, 303(1): 1-10 (2002).
Database Beilstein Beilstein GmbH; XP002398257, BRN = 6821289 & Itakura et al., Biosci. Biotechnol. Biochem., 58: 488-493 (1994) (Abstract).
Database Beilstein Beilstein GmbH; XP002398258, BRN = 7045819 & Gellerman, et al., Tetrahedron, 50: 12959-12972 (1994) (Abstract).
Database Beilstein Beilstein GmbH; XP002398259, BRN = 2661821 & Sakiyama et al., Chem. Lett., 893 (1978) (Abstract).
Database Beilstein Beilstein GmbH; XP002398260, BRN = 2154476 & Dalgliesch, J. Chem. Soc., 137: 140 (1952) (Abstact).
Database Beilstein Beilstein GmbH; XP002398261, BRN = 8692551 & Moon, Byoungho, et al., Tetrahedron, 56: 9057-9062 (2000) (Abstract). Database Beilstein Beilstein GmbH; XP002398262, BRN = 9065890 & Camacho, et al., J. Med. Chem., 45: 263-274 (2002) (Abstract).
Database Beilstein Beilstein GmbH; XP002398263, BRN = 5085110 & Bolognese, et al., J. Heterocycl. Chem., 25: 1247-1250 (1988) (Abstract).
Database Beilstein Beilstein GmbH; XP002398264, BRN = 5354529 & Itakura, et al., Tetrahedron Lett., 33: 2567-2570 (1992) (Abstract).
Database Beilstein Beilstein GmbH; XP002398265, BRN = 5873250 & Gellerman, et al., Synthesis, 3: 239-241 (1994) (Abstract).
Database Beilstein Beilstein GmbH; XP002398266, BRN = 2216769 & Tsuji, et al., Bull. Chem. Soc. Jpn., 54: 2369-2373 (1981) (Abstact).
Database Beilstein Beilstein GmbH; XP002398267, BRN = 2732633 & Back, Arch. Pharm. (Weinheim Ger.), 305: 448 (1972) (Abstract).
Database Beilstein Beilstein GmbH; XP002398268, BRN = 2802772 & Butenandt, et al., Naturforsch., 8b: 454, 461 (1953) (Abstract).

(Continued)

*Primary Examiner* — Brian J Davis
(74) *Attorney, Agent, or Firm* — Rothwell, Figg, Ernst & Manbeck, P.C.

(57) ABSTRACT

The invention relates to 2-aminobenzoyl-alkylamines, -alkylamides and -alkylthioamides, and their application for treatment or prevention of various physiological conditions.

9 Claims, No Drawings

OTHER PUBLICATIONS

Database Beilstein Beilstein GmbH; XP00239869, BRN = 2940161 & Back, Arch. Pharm., 305: 448 (1972) (Abstract).

Database Beilstein Beilstein GmbH; XP002398270, XP002398270, BRN=2093152 & Joh, J. Biochem., 58: 248 (1965) (Abstract).

Database Beilstein Beilstein GmbH; XP002398272, BRN= 3710916 & Senoheld, J. Inst. Polyteh., 5: 198, 199 (1956) (Abstract).

Database Beilstein Beilstein GmbH; XP002398273, BRN = 2733318 & Runti et al., Boll. Chim. Farm. 103: 165, 167 (1964) (Abstract).

Rivett, D., et al., "Formation of Substituted 1-Benzazepine-2,5-diones from Derivatives of Kynurenine," Australian Journal of Chemistry, 31(2): 439-43, CODON: AJCHAS; ISSN: 0004-9425, 1978, XP008068823.

J. León, et al., "Modification of Nitric Oxide Synthase Activity and Neuronal Response in Rat Striztum by Melatonin and Kynurenine Derivatives," Journal of Neuroendocrinology, 1998, vol. 10, 297-302.

K. Görlitzer, et al., "10H-Indolo[3,2-b]chinoline," Archiv der Pharmazie, vol. 314, No, 10, Oct. 1981, 12 pages.

Abstract of KG Charlton et al., "Cardiovascular actions of kynuramine and 5-hydroxykynuramine in pithed rats," Journal of Neural Transmission 1983; 57(4): 199-211.

Translation of Korean Notification of Preliminary Rejection, issued in 10-2005-7025006 on Mar. 11, 2011, 7 pages.

* cited by examiner

2-AMINOBENZOYL DERIVATIVES

This application is a filing under 35 USC 371 of PCT/IL2004/000567, filed Jun. 24, 2004 and claims priority from Israeli application number 156669, filed Jun. 26, 2003.

FIELD OF THE INVENTION

The present invention relates to novel 2-aminobenzoyl derivatives, pharmaceutical formulations containing them, and use of the compounds in the manufacture of medicaments for treating or preventing various diseases.

BACKGROUND OF THE INVENTION

The present invention relates generally to novel compounds, their use in therapy, and pharmaceutical formulations containing them.

The amino acid tryptophan is converted biologically through the "kynurenine pathway" (Beadle, G. W., Mitchell, H. K., and Nyc, J. F., Proc. Nat. Acad. S C., 33, 155 (1948); see Charles Heidelberger, Mary E. Gullberg, Agnes Fay Morgan, and Samuel Lepkovsky TRYPTOPHAN METABOLISM. I. CONCERNING THE MECHANISM OF THE MAMMALIAN CONVERSION OF TRYPTOPHAN INTO KYNURENINE, KYNURENIC ACID, AND NICOTINIC ACID. J. Biol. Chem. (1949) 179: 143-150). Over 95% of all dietary tryptophan is metabolized to kynurenines (Wolf, H.—Studies on tryptophan metabolism in man. Scand J Clin Lab Invest 136(suppl.): 1-186, 1974). In peripheral tissues, in particular the liver, the indole ring of tryptophan is modified by either tryptophan dioxygenase or indoleamine 2,3-dioxygenase, which results in the formation of formylkynurenine. Kynurenine formylase then rapidly converts formylkynurenine to L-kynurenine, which is the key compound in the kynurenine pathway (W. Eugene Knox and Alan H. Mehler THE CONVERSION OF TRYPTOPHAN TO KYNURENINE IN LIVER. I. THE COUPLED TRYPTOPHAN PEROXIDASE-OXIDASE SYSTEM FORMING FORMYLKYNURENINE J. Biol. Chem. (1950)187: 419-430). L-kynurenine is present in low concentrations in the blood, the brain and in peripheral organs and it can easily cross the blood-brain barrier through the large neutral amino acid carrier. L-kynurenine is metabolized by three different enzymes in mammalian tissues: kynurenine 3-hydroxylase which form 3-hydroxy-kynurenine (3-HK); kynureninase which forms anthranilic acid and kynurenine aminotransferase (KAT) which causes the formation of kynurenic acid. 3-HK is metabolized by the same KAT to yield xanthurenic acid, a metabolically inert side product of the pathway, or by kynureninase to give rise to 3-hydroxyanthranilic acid, which is eventually converted to quinolinic acid. Finally, quinolinic acid is metabolized by quinolinic acid phosphoribosyltransferase, yielding nicotinic acid mononucleotide and subsequent degradation products including the end product $NAD^+$.

Kynurenic acid, 3-hydroxykynurenine and quinolinic acid are all neuroactive intermediates of this catabolic cascade. 3-hydroxykynurenine is a free radical generator, which has been shown to cause induction of apoptosis, potentiation of excitotoxicity, cataract formation, neurodegenerative diseases, stroke, traumatic injury, neurovirological diseases and neuroinflammation. Quinolinic acid is an N-methyl-D-aspartate (NMDA) receptor agonist and free radical generator, and as such it can cause excitotoxicity, neurodegenerative diseases, stroke, traumatic brain injury, epilepsy, cerebral malaria, perinatal hypoxia, neurovirological diseases and neuroinflammation. Endogenous quinolinic acid might lead to NMDA receptoractivation to promote excitotoxicity and neurotoxicity leading to physiological and pathological processes that are mediated by NMDA receptors. Among the three neuroactive kynurenines, kynurenic acid (KYNA) has recently received the most attention. First described as a neuroinhibitory compound two decades ago, KYNA, at high, nonphysiological, concentrations is a broad-spectrum antagonist of ionotropic glutamate receptors. High concentrations of KYNA are anticonvulsant and provide excellent protection against excitotoxic injury. At much lower concentrations, KYNA acts as a competitive blocker of the glycine coagonist site of the NMDA receptor and as a noncompetitive inhibitor of the α7 nicotinic acetylcholine receptor. The fact that the affinity of KYNA to these two $Ca^{2+}$-permeable receptors is in the range of KYNA levels in the human brain and reasonably close to the (lower) KYNA content of the rodent brain suggests a physiological function in glutamatergic and cholinergic neurotransmission. Direct support for such a role has been provided, for example, by in vivo studies in the rat striatum where a reduction in KYNA levels enhances vulnerability to an excitotoxic insult and, conversely, modest elevations of KYNA inhibit glutamate release (Schwarcz R, Pellicciari R. Manipulation of brain kynurenines: glial targets, neuronal effects, and clinical opportunities. *J Pharmacol Exp Ther.* 2002 : 303:1-10).

Since kynurenines have been suggested to participate not only in the pathophysiology of neurodegenerative and seizure disorders, but also to play a role in a large number of etiologically diverse CNS diseases, it is important to modulate their formation. We propose that the 2-aminobenzoyl derivatives (kynurenine-like compounds) described here will be useful for such therapeutic intervention. Suggested mechanism of action could be, but is not limited to, by inhibiting enzymes in the kynurenine pathway, and/or inhibiting intermediate compounds, and/or inhibiting free radical formation.

SUMMARY OF THE INVENTION

The present invention is directed to compounds having the formula (I):

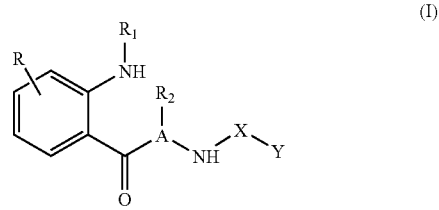

(I)

wherein R, $R_1$, $R_2$, A, X and Y are as defined below, and to stereoisomers and pharmacologically acceptable salts thereof.

The invention further is directed to pharmaceutical formulations comprising such compounds and to the administration of such compounds and formulations as therapeutic agents.

DETAILED DESCRIPTION OF THE INVENTION

The invention relates to compounds having the formula (I):

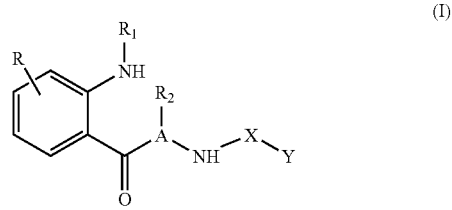

(I)

and stereoisomers and pharmaceutically acceptable salts thereof, wherein:

A is $C_{1-6}$alkylene; R, $R_1$ and $R_2$ are independently hydrogen, halo, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamido, guanidine, amidino, acylamido, hydroxy, thiol, acyloxy, azido, alkoxy, carboxy, carbonylamido, S-alkyl or alkylyhiol; X is >$C_{1-6}$ alkylene, >C=O or >C=S or a single bond; and Y is hydrogen, halo, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamido, guanidine, amidino, acylamido, hydroxy, thiol, acyloxy, azido, alkoxy, carboxy, carbonylamido styryl which may be ring-substituted by up to four substituents independently selected from among hydrogen, halo, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamido, guanidine, amidino, acylamido, hydroxy, thiol, acyloxy, azido, alkoxy, S-alkyl, alkylyhiol or —COQ, where Q is hydroxy, $C_{1-6}$alkoxy, amino, mono-$C_{1-6}$ alkylamino, di-$C_{1-6}$ alkylamino, hydroxylamino, $C_{1-4}$ alkoxyamino or aryl-$C_{1-4}$-alkoxyamino, but excluding (a) the compounds where simultaneously X is >C=O, Y is methyl, A is $CH_2CH_2$, R is 5-methoxy, $R_1$ is H or formyl and $R_2$ is H, and (b) the compounds where the moiety -A($R_2$)—NH—X—Y is —$CH_2CH(COQ)$—$NH_2$ or —CH(haloalkyl)—CH(COQ)—$NH_2$., and (c) the compounds where simultaneously X is a single bond, Y is arylalkyl, A is $CH_2CH_2CH_2$, both $R_1$ and $R_2$ are H and R is 4-halo where the moiety —CO-A($R_2$)—NH—X—Y is deemed to be in the 1-position of the depicted benzene ring.

Without prejudice to the generality of the compounds of the present invention, a sub-group of presently preferred compounds (formula II) is defined by the facts that R is hydrogen, methyl or methoxy, $R_1$ is hydrogen or formyl, $R_2$ is hydrogen or carboxyl, and $R_3$ is hydrogen, halo, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamide, guanidine, amidino, acylamido, hydroxy, thiol, acyloxy, azido, alkoxy, carboxy, carbonylamido, S-alkyl or alkylyhiol, and stereoisomers and pharmaceutically acceptable salts thereof.

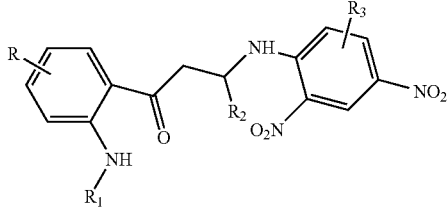

(II)

Another sub-group of the present compounds is defined by the facts that in the formula (I) X is 2-furyl, 2-dihydrofuryl, 2-tetrahydrofuryl or (2-R°—COO—)phenyl, any of which may be substituted by 1-2 substituents selected from $C_{1-4}$ alkyl, $C_{1-4}$alkoxy, OH, nitro, and Y is hydrogen or styryl which is ring-substituted by up to two substituents independently selected from among halogen, $C_{1-4}$alkyl, $C_{1-4}$ alkoxy, OH, nitro, aryl, aryl-$C_{1-4}$ alkyl, or aryl-$C_{1-4}$ alkoxy, and stereoisomers and pharmaceutically acceptable salts thereof.

"Aryl" in the present specification and claims means a monovalent radical derived from an aromatic compound by removing a hydrogen atom from the aromatic nucleus.

The present invention includes within its scope also the pharmaceutical formulations containing as an active substance a therapeutically effective amount of a compound of formula (I) or a pharmaceutically acceptable salt thereof as well as any possible isomer, or mixture of isomers, covered by the formula (I) in association with one or more pharmaceutically acceptable diluents, preservatives, solubilizers, emulsifiers, adjuvants, excipients and carriers, particularly those conventionally used in pharmaceutical and veterinary formulations. The present pharmaceutical formulations may be adapted for administration to humans and/or animals.

The compounds of formula (I) are useful for treating and/or preventing, and/or minimizing neuronal loss associated with stroke, ischemia, CNS trauma, hypoglycemia and surgery, CNS disorders including neurodegenerative diseases such as Alzheimer's disease, amyotrophic lateral sclerosis, Huntington's disease, Parkinson's disease and Down's syndrome, treating or preventing the adverse consequences of the over stimulation of the excitatory amino acids, psychiatric disorders, e.g., sleep disorders, epilepsy and other convulsive disorders, anxiety, psychiatric diseases, psychosis, senile dementia, multi-infarct dementia, chronic pain (analgesia), glaucoma, CMV retinitis, urinary incontinence, and inducing anesthesia, as well as enhancing cognition, and preventing opiate tolerance and withdrawal symptoms.

By way of further elaboration or explanation of conditions which it is presently contemplated may be amenable to treatment by administration of the present compounds, such conditions include impotence; cardiovascular disorders including hypertension, preventing blood coagulation, anti-inflammation, neuropathy, chronobiological-based disorders, e.g., jet lag, circadian sleep disorders such as delayed sleep syndrome, shift-work problems, and seasonal-related disorders, e.g. seasonal affective disorder (SAD); endocrine indications, e.g., contraception and infertility, precocious puberty, premenstrual syndrome, hyperprolactinemia, and growth hormone deficiency; neoplastic diseases including e.g. cancer and other proliferative diseases (benign and tumor prostate growth), immune system disorders including AIDS, conditions associated with senescence, ophthalmological diseases, cluster headache, migraine, skin-protection, diabetes stabilization and weight gain disorders (leptin, obesity), and as an aid to animal breeding, e.g., regulation of fertility, puberty, pelage color.

Without prejudice to the generality of the compounds of the present invention, in addition to sub-groups already mentioned above, another sub-group of presently preferred compounds is defined by the facts that in formula (I), X is a 2,4-dinitrophenyl group, A is $CH_2CH_2$ or $CH_2CHCOOH$ and $R_2$ and Y are each hydrogen.

Another sub-group of the present compounds is defined by the facts that in formula (I), $R_2$ is hydrogen and at least one of the following conditions applies, namely: R is 5-methoxy; and/or A is $CH_2CH_2$ or $CH_2CHCOOH$, and within these sub-groups, $R_1$ is preferably also hydrogen. Illustrative combinations of X and Y in compounds of the invention, particularly where $R_1$=H, are the following:

X is —CO— and Y is 2-furyl; or
X is —CO— and Y is 2-tetrahydrofuryl; or
X is —$CH_2$— and Y is 2-tetrahydrofuryl; or
X is —CO— and Y is 2-acetoxyphenyl; or
X is —CO— and Y is 3,4-dihydroxystyryl or 3,4-dihydroxycinnamoyloxy.

The present invention also includes within its scope pharmaceutical formulations containing as an active substance a therapeutically effective amount of a compound of formula (I) or a pharmaceutically acceptable salt thereof as well as any possible isomer, or mixture of isomers, covered by the formula (I) in association with one or more pharmaceutically acceptable diluents, preservatives, solubilizers, emulsifiers, adjuvants, excipients and carriers, particularly those conventionally used in pharmaceutical and veterinary formulations. The present pharmaceutical formulations may be adapted for administration to humans and/or animals.

The pharmaceutical formulation according to the invention is preferably characterized by at least one of the following features:

(i) it is adapted for oral, rectal, parenteral, transbuccal, intrapulmonary (e.g. by inhalation) or transdermal administration;

(ii) it is in unit dosage form, each unit dosage comprising an amount of said at least one member which lies within the range of 0.0025-1000 mg;

(iii) it is a controlled release formulation, wherein said at least one member is released at a predetermined controlled rate.

For oral administration, the pharmaceutical formulations may be utilized as e.g. tablets, capsules, emulsions, solutions, syrups or suspensions. For parenteral administration, the formulations may be utilized as ampoules, or otherwise as suspensions, solutions or emulsions in aqueous or oily vehicles. The need for suspending, stabilizing and/or dispersing agents will of course take account of the fact of the solubility or otherwise of the active compounds, in the vehicles that are used in particular embodiments. The formulations may additionally contain e.g. physiologically compatible preservatives and antioxidants. In the formulations for topical application, e.g. creams, lotions or pastes, the active ingredient may be mixed with conventional oleaginous or emulsifying excipients.

The pharmaceutical formulations may also be utilized as suppositories with conventional suppository bases such as cocoa butter or other glycerides. Alternatively, the formulations may be made available in a depot form which will release the active formulation slowly in the body, over a pre-selected time period. Moreover, the compounds of the invention may be administered by using transbuccal, intrapulmonary or transdermal delivery systems.

Also combinations of the compounds of formula I as well as their salts with other active ingredients, especially other neuroleptics, thymoleptics, anxiolitics, tranquilizers, analgetics, antiparkinson's drugs (dopaminergic and non-dopaminergic drugs) or the like, fall within the scope of the present invention.

The compounds of the present invention are useful for treating and/or preventing, and/or minimizing neuronal loss associated with stroke, ischemia, CNS trauma, hypoglycemia and surgery, CNS disorders including neurodegenerative diseases such as Alzheimer's disease, amyotrophic lateral sclerosis, Huntington's disease, Parkinson's disease and Down's syndrome, treating or preventing the adverse consequences of the overstimulation of the excitatory amino acids, psychiatric disorders, e.g., sleep disorders, epilepsy and other convulsive disorders, anxiety, psychiatric diseases, psychosis, senile dementia, multi-infarct dementia, chronic pain (analgesia), glaucoma, CMV retinitis, urinary incontinence, and inducing anesthesia, as well as enhancing cognition, and preventing opiate tolerance and withdrawal symptoms.

By way of further elaboration or explanation of conditions which it is presently contemplated may be amenable to treatment by administration of the present compounds, such conditions include impotence; cardiovascular disorders including hypertension, preventing blood coagulation, anti-inflammatory, neuropathy, chronobiological-based disorders, e.g. jet lag, circadian sleep disorders such as delayed sleep syndrome, shift-work problems, and seasonal-related disorders, e.g. seasonal affective disorder (SAD); endocrine indications, e.g., contraception and infertility, precocious puberty, premenstrual syndrome, hyperprolactinemia, and growth hormone deficiency; neoplastic diseases including e.g. cancer and other proliferative diseases (benign and tumor prostate growth); immune system disorders including AIDS; conditions associated with senescence; ophthalmological diseases; cluster headache, migraine; skin-protection, diabetes stabilization and weight gain disorders (leptin, obesity), and as an aid to animal breeding, e.g., regulation of fertility, puberty, pelage color.

The invention will be illustrated by the following Examples. The following examples are understood to be illustrative only and are not intended to limit the scope of the present invention in any way.

EXAMPLE 1

2-(2-aminobenzoyl)-N-(2,4-dinitrophenyl)ethylamine

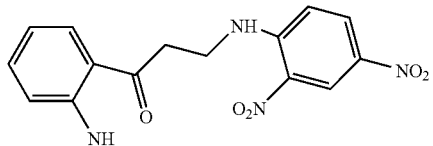

Kynuramine 2HBr (125 mg) is dissolved in 5 cc of absolute ethanol in a 50 cc flask. A solution of 2,4-dinitrofluorobenzene, 71 mg in EtOH 5 cc is then added (a clear yellow solution is formed). After five minutes, 2 cc of a 10% $NaHCO_3$ solution are introduced drop-wise in the flask. The reaction is left at room temperature overnight. The following morning the formed light yellow precipitate is filtered, washed with water and ethanol and dried in UHV obtaining 80 mg of product (approx. yield 63%).

EXAMPLE 2

3-(2-aminobenzoyl)-2-(2,4-dinitroanilino)propanoic acid

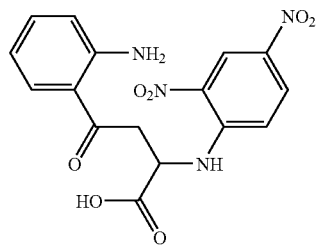

L-Kynurenine (125 mg) is dissolved in 5 cc of absolute ethanol in a 50 cc flask. A solution of 2,4-dinitrofluorobenzene, 71 mg in EtOH 5 cc is then added (a clear yellow solution is formed). After five minutes, 2 cc of a 10% $NaHCO_3$ solution are introduced drop-wise in the flask. The reaction is left at room temperature overnight. The following morning the formed light yellow precipitate is filtered, washed with water and ethanol and dried in UHV obtaining 80 mg of product (approx. yield 71%).

The invention includes also pharmaceutically acceptable salts of the compounds of formula (I), as well as the possible isomers covered by the formula (I) both separately and in admixture.

BIOLOGICAL TESTING OF COMPOUNDS OF THE INVENTION

Experiment 1:

Evaluation of the anti-Parkinsonian activity using MPTP-treated mice with/without a subthreshold dose of L-Dopa Animals: six month old male C57 BL/6 mice, weighing 22-25 g were used. Following arrival at the laboratory, the mice were allowed to acclimatise for two weeks in a room with controlled temperature (21±1° C.), and a constant light-dark schedule (12 hr on/12 hr off, lights on between 06.00 and 18.00 hrs). Free access to food and water was maintained throughout. They were housed in groups of 12 animals and tested only during the hours of light (08.00-15.00 hrs). All testing was performed in a normally lighted room. Each test chamber (i.e. activity test cage) was placed in a soundproofed wooden box with 12 cm thick walls and front panels and had dimmed lighting.

Behavioral measurements and apparatus: An automated device, consisting of macrolon rodent test cages (40×25×15 cm) each placed within two series of infra-red beams (at two different heights, one low and one high, 2 and 8 cm, respectively, above the surface of the sawdust, 1 cm deep), was used to measure spontaneous and/or drug-induced motor activity of MPTP and control mice. The following parameters were measured: LOCOMOTION was measured by the low grid of infrared beams. Counts were registered only when the mouse in the horizontal plane, ambulating around the test-cage. REARING was registered throughout the time when at least one high level beam was interrupted, i.e. the number of counts registered was proportional to the amount of time spent rearing. TOTAL ACTIVITY was measured by a sensor (a pick-up similar to a gramophone needle, mounted on a lever with a counterweight) with which the test cage was constantly in contact. The sensor registered all types of vibration received from the test cage, such as those produced both by locomotion and rearing as well as shaking, tremors, scratching and grooming.

Behavioral measurements (locomotion, rearing and total activity): Twelve days after MPTP injections (2×40 mg/kg, s.c., 24 hr interval), the mice were injected i.p with 2-(2-aminobenzoyl)-N-(2,4-dinitrophenyl)ethylamine (0.3, 1, 3, 10 mg/kg) or vehicle (10% DMSO, 1% CMC) and immediately thereafter placed in the activity test chambers and their motor behaviour were monitored for 60 min. After 60 min, the mice were injected with 5 mg/kg L-Dopa (s.c) and then replaced in the test chamber and activity measurements maintained for a further 240 min. Each dose was separated by two days, starting from the lowest dose.

Table 1 presents the mean (± standard deviations) locomotion, rearing and total activity counts of MPTP-treated and control mice administered either 2-(2-aminobenzoyl)-N-(2, 4-dinitrophenyl)ethylamine or vehicle administered with a subthreshold dose of L-Dopa. 1 % level of significance is represented by an asterisk (Tukey HSD test).

| TREATMENT | LOCO-MOTION | REARING | TOTAL ACTIVITY |
|---|---|---|---|
| Vehicle | 1000 ± 145 | 920 ± 181 | 10937 ± 2812 |
| MPTP + vehicle | 200 ± 90 | 225 ± 72 | 4530 ± 937 |
| MPTP + 0.3 mg/kg 2-(2-aminobenzoyl)-N-(2,4-dinitrophenyl)ethylamine | 273 ± 64 | 290 ± 73 | 5160 ± 1093 |
| MPTP + 1 mg/kg 2-(2-aminobenzoyl)-N-(2,4-dinitrophenyl)ethylamine | 473 ± 108* | 582 ± 145* | 6250 ± 625* |
| MPTP + 3 mg/kg 2-(2-aminobenzoyl)-N-(2,4-dinitrophenyl)ethylamine | 510 ± 107* | 731 ± 110* | 6563 ± 781* |
| MPTP + 10 mg/kg 2-(2-aminobenzoyl)-N-(2,4-dinitrophenyl)ethylamine | 470 ± 110* | 619 ± 102* | 6250 ± 625* |

2-(2-aminobenzoyl)-N-(2,4-dinitrophenyl)ethylamine had no effect at any dose the first 60-min period before L-Dopa, as compared to the MPTP-treated vehicle mice. However, 2-(2-aminobenzoyl)-N-(2,4-dinitrophenyl)ethylamine improved significantly all three behavioural parameters when administered together with a subthreshlod dose of L-Dopa. 2-(2-aminobenzoyl)-N-(2,4-dinitrophenyl) ethylamine (1, 3 or 10 mg/kg) improved significantly the locomotion, rearing and total activity of MPTP-treated mice, as compared to the MPTP vehicle group.

2-(2-aminobenzoyl)-N-(2,4-dinitrophenyl)ethylamine administered to vehicle control animals had no effects in any variable.

Experiment 2:

Electrophysiological characterisation of NMDA-activated currents in freshly isolated hippocampal neurones of rat.

Isolation of hippocampal neurons: Wistar rats (12-14 days) were decapitated without anaesthesia and the hippocampus was removed. It was manually cut into slices (0.2-0.4 mm), in a solution containing (mM): 150 NaCl; 5 KCl; 1.25 $NaH_2PO_4$; 2 $CaCl_2$; 2 $MgCl_2$; 26 $NaHCO_3$; 20 glucose. Slices were preincubated in this solution for 30 min at room temperature. The enzymatic treatment proceeded in the same solution with lower Ca2+ concentration (0.5 mm) containing 0.4 mg/ml protease from *aspergillus oryzae*. The incubation in the enzyme solution proceeded at 32° C. within 10 min. Slices were kept subsequently in enzyme-free solution containing normal Ca2+ concentration and used within 6-8 h for obtaining isolated neurons. Throughout the entire procedure the solutions were continuously saturated with a 95% $O_2$ and 5% $CO_2$ gas mixture to maintain pH 7.4. For cell dissociation the slice was transferred into the extracellular solution containing (mM): 150 NaCl; 5 KCl; 2 $CaCl_2$; 10 N-2-hydroxyethylpiperazine-N'-2-ethanesulphonic acid (Hepes); pH adjusted with NaOH to 7.4. Single cells were isolated from CA and CA3 zones of hippocampal slices by vibrodissociation method. They had diameter 10-15 m and preserved a small part of dendritic tree. After isolation they were usually suitable for recording for 1-2 h.

Salines and chemicals: The contents of the extracellular solution was as follows (in mM): 130 NaCl, 5 KCl, 2 $CaCl_2$, 20 N-2-hydroxyethylpiperazine-N'-2-ethansulfonic acid (Hepes); 0.1 μm TTX, 10 μm glycine, 300 μm l-aspartate; pH was adjusted with NaOH to 7.4.

The contents of the intracellular solution were as follows (in mM): 110CSF, 20Tris-HCl (ph=7.2). L-aspartate and glycine solutions were prepared on the day of experiment.

The tested substance 2-(2-aminobenzoyl)-N-(2,4-dinitrophenyl)ethylamine was dissolved in DMSO.

Current recording and data analysis: The drug-containing solutions were applied by the fast "concentration clamp" method using "jumping table" set-up (Pharma Robot, Kiev). The currents were recorded with patch clamp technique in the whole-cell configuration. Recording of the currents was performed using EPC-7 L/M patch-clamp amplifier.

NMDA-activated currents: The currents were filtered at 3 kHz (three-pole active Bessel filter) digitally sampled at the rate 6000 pts per point for NMDA activated currents. NMDA-induced transmembrane currents were measured in the presence of 10 μM glycine and 300 μM L-aspartate in the control and test solutions. The currents were recorded at holding potential −70 mV.

Calculations: The inhibition of current at different concentrations of the substance was averaged at least for 4 cells. The effect of substance was measured as the mean ratio I/Io where I was the current under the action of substance and Io was the current in control conditions. S.D. represents standard deviation.

The action of 10 μM 2(2-aminobenzoyl)-n-2,4-dinitrophenylethylamine on NMDA-activated currents:

|  | INDIVIDUAL CELLS: I/I₀ | | | | |
| --- | --- | --- | --- | --- | --- |
|  | 1 | 2 | 3 | Mean | ± SD |
| 2-(2-aminobenzoyl)-N-(2,4-dinitrophenyl)ethylamine 10 mM | 9277 | 7715 | 8017 | 8336 | 828 |

This experiment revealed that 2-(2-aminobenzoyl)-N-(2,4-dinitrophenyl)ethylamine has a blocking activity on NMDA receptors.

The invention claimed is:

1. A compound having the formula (I):

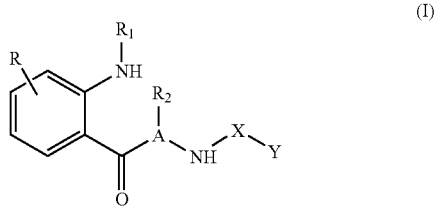

(I)

or a stereoisomer or a pharmaceutically acceptable salt thereof, wherein:

A is $C_{1-6}$ alkylene; R is hydrogen, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamido, guanidine, amidino, acylamido, hydroxy, thiol, acyloxy, azido, alkoxy, carboxy, carbonylamido, S-alkyl or alkylthiol, $R_1$ and $R_2$ are independently hydrogen, halo, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamido, guanidine, amidino, acylamido, hydroxy, thiol, acyloxy, azido, alkoxy, carboxy, carbonylamido, S-alkyl or alkylthiol, X is $>C_{1-6}$ alkylene, $>C=O$ or $>C=S$ or a single bond; and Y is halo, a heterocyclic group, alkenyl, alkynyl, arylalkyl, arylalkynyl, hydroxyalkyl, nitro, amino, cyano, cyanamido, guanidine, amidino, acylamido, hydroxy, thiol, azido, carboxy, carbonylamido, or styryl, wherein where Y is a ring it may be ring-substituted by up to four substituents independently selected from among hydrogen, halo, haloalkyl, aryl, a heterocyclic group, a heteroaryl group, alkyl, alkenyl, alkynyl, arylalkyl, arylalkenyl, arylalkynyl, hydroxyalkyl, nitro, amino, cyano, cyanamido, guanidine, amidino, acylamido, hydroxy, thiol, acyloxy, azido, alkoxy, S-alkyl, alkylthiol, or —COQ, where Q is hydroxy, $C_{1-6}$ alkoxy, amino, mono- $C_{1-6}$ alkylamino, di- $C_{1-6}$ alkylamino, hydroxylamino, $C_{1-4}$ alkoxyamino or aryl-$C_{1-4}$-alkoxyamino.

2. A compound according to claim 1, or a stereoisomer or pharmaceutically acceptable salt thereof, where in formula (I), $R_2$ is hydrogen and at least one of the following conditions applies, namely:
R is 5-methoxy; or
A is $CH_2CH_2$ or
$R_1$ is hydrogen.

3. 2-(2-aminobenzoyl)-N-(2,4-dinitrophenyl)ethylamine, or a pharmaceutically acceptable salt thereof.

4. A pharmaceutical formulation containing a therapeutically effective amount of at least one compound as defined in claim 1 in association with at least one pharmaceutically acceptable ingredient selected from diluents, preservatives, solubilizers, emulsifiers, adjuvants, excipients and carriers.

5. A pharmaceutical formulation according to claim 4, which is further characterized by at least one of the following features:
  (i) it is adapted for oral, rectal, parenteral, transbuccal, intrapulmonary or transdermal administration;
  (ii) it is in unit dosage form, each unit dosage comprising an amount of said at least one compound which lies within the range of 0.0025-1000 mg;
  (iii) it is a controlled release formulation, wherein said at least one compound is released at a predetermined controlled rate;
  (iv) it comprises additionally at least one known therapeutically active ingredient selected from neuroleptics, thymoleptics, anxiolitics, tranquilizers, analgesics, and anti-parkinson's drugs.

6. A method of treating a subject suffering from a physiological condition selected from the group consisting of stroke, ischemia, CNS trauma, hypoglycemia and surgery, CNS disorders, overstimulation of the excitatory amino acids, psychiatric disorders, epilepsy or other convulsive disorder, anxiety, psychosis, senile dementia, multi-infarct dementia, chronic pain (analgesia), glaucoma, CMV retinitis, urinary incontinence, impotence, cardiovascular disorders, blood coagulation, neuropathy, anti-inflammatory, chronobiological-related disorders, seasonal-related disorders, endocrine indications, precocious puberty, premenstrual syndrome, hyperprolactinemia, growth hormone deficiency, neoplastic disease, benign or tumor prostate growth, immune system disorders, conditions associated with senescence, ophthalmological diseases, cluster headache, migraine, or weight gain disorders, which comprises administering a therapeutically effective amount of a compound of formula I or a stereoisomer or a pharmaceutically acceptable salt thereof as defined in claim 1.

7. The method of claim 6, wherein said compound or stereoisomer or salt is administered in association with at least one pharmaceutically acceptable ingredient selected from diluents, preservatives, solubilizers, emulsifiers, adjuvants, excipients and carriers.

8. The method of claim 7, wherein said pharmaceutical formulation is further characterized by at least one of the following features:
  (i) it is adapted for oral, rectal, parenteral, transbuccal, intrapulmonary or transdermal administration;
  (ii) it is in unit dosage form, each unit dosage comprising an amount of said at least one compound which lies within the range of 0.0025-1000 mg;
  (iii) it is a controlled release formulation, wherein said at least one compound is released at a predetermined controlled rate;
  (iv) it comprises additionally at least one known therapeutically active ingredient selected from neuroleptics, thymoleptics, anxiolitics, tranquilizers, analgesics, and anti-Parkinson's drugs.

9. A method for regulating fertility, puberty or pelage color in animal breeding, which comprises administering to a breeding animal an effective amount of a compound of formula I or a stereoisomer or pharmaceutically acceptable salt as defined in claim 1.

* * * * *